United States Patent [19]
Muller et al.

[11] Patent Number: 5,874,448
[45] Date of Patent: Feb. 23, 1999

[54] SUBSTITUTED 2-(2,6 DIOXO-3-FLUOROPIPERIDIN-3-YL)-ISOINDOLINES AND METHOD OF REDUCING TNFα LEVELS

[75] Inventors: George W. Muller, Bridgewater; David I. Stirling, Branchburg; Roger Shen-Chu Chen, Edison; Hon-Wah Man, Neshanic Station, all of N.J.

[73] Assignee: Celgene Corporation, Warren, N.J.

[21] Appl. No.: 976,140

[22] Filed: Nov. 18, 1997

[51] Int. Cl.$^6$ ....................... A61K 31/445; C07D 401/04
[52] U.S. Cl. .............................................. 514/323; 546/201
[58] Field of Search .............................. 546/201; 514/323

[56] References Cited

U.S. PATENT DOCUMENTS

| | | | |
|---|---|---|---|
| 5,385,901 | 1/1995 | Kaplan | 514/231.5 |
| 5,635,517 | 6/1997 | Muller | 514/323 |
| 5,798,368 | 8/1998 | Muller | 514/323 |

*Primary Examiner*—Evelyn Huang
*Attorney, Agent, or Firm*—Mathews, Collins, Shepherd & Gould, P.A.

[57] ABSTRACT

1-Oxo-2-(2,6-dioxo-3-fluoropiperidin-3-yl)isoindolines and 1,3-dioxo-2-(2,6-dioxo-3-fluoropiperidin-3-yl)isoindolines reduce the levels of TNFα in a mammal. A typical embodiment is 1,3-dioxo-2-(2,6-dioxo-3-fluoropiperidin-3-yl)-isoindoline.

23 Claims, No Drawings

SUBSTITUTED 2-(2,6 DIOXO-3-FLUOROPIPERIDIN-3-YL)-ISOINDOLINES AND METHOD OF REDUCING TNFα LEVELS

The present invention relates to 2-(2,6-dioxo-3-fluoropiperidin-3-yl)-isoindolines, the method of reducing levels of tumor necrosis factor α in a mammal through the administration thereof, and pharmaceutical compositions of such derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662–664 (1987) and Hinshaw et al., Circ. Shock 30, 279–292 (1990)}; cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516–518 (1986) and Johnson et al., Endocrinology 124(3), 1424–1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3–10 (1990)}. In Graft versus Host Reaction, increased serum TNFα levels have been associated with major complication following acute allogenic bone marrow transplants {Holler et al., Blood, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586–1591 (1989)}.

Macrophage-induced angiogenesis TNFα is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339–343, and Koch, Progress in Medicinal Chemistry, 22, 166–242 (1985)).

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344, 245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughinan et al., J. Lab. Clin. Med. 115(1), 36–42 (1990)}.

TNFα is also implicated in the inflammatory response which follows reperfusion, called reperfusion injury, and is a major cause of tissue damage after loss of blood flow {Vedder et al., PNAS, 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin (Sherry et al., J. Cell Biol 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(1), 121–132 (1989)}.

TNFα blockage with monoclonal anti-TNFα antibodies has been shown to be beneficial in rheumatoid arthritis {Elliot et al., Int. J. Pharmac. 1995 17(2), 141–145). High levels of TNFα are associated with Crohn's disease {von Dullemen et al., Gastroenterology, 1995 109(1), 129–135} and clinical benefit has been acheived with TNFα antibody treatment.

Moreover, it now is known that TNFα is a potent activator of retrovirus replication including activation of HIV-1. (Duh et al., Proc. Nat. Acad. Sci. 86, 5974–5978 (1989); Poll et al., Proc. Nat. Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad. Sci.*, 87, 782–784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osbom, et al., *PNAS* 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762–66; Duh et al., *Proc. Natl. Acad. Sci.* 1989, 86, 5974–78; Bachelerie et al., *Nature* 1991, 350, 709–12; Boswas et al., *J. Acquired Immune Deficiency Syndrome* 1993, 6, 778–786; Suzuki et al., *Biochem. And Biophys. Res. Comm.* 1993, 193, 277–83; Suzuki et al., *Biochem. And Biophys. Res Comm.* 1992, 189, 1709–15; Suzuki et al., *Biochem. Mol. Bio. Int.* 1993, 31(4); 693–700; Shakhov et al., *Proc. Natl. Acad. Sci. USA* 1990, 171, 35–47; and Staal et al., *Proc. Natl. Acad. Sci. USA* 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3', 5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. Phosphodiesterases control the level of cAMP through hydrolysis and inhibitors of phosphodiesterases have been shown to increase cAMP levels.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383 }.

DETAILED DESCRIPTION

The present invention is based on the discovery that certain classes of non-polypeptide compounds more fully described herein decrease the levels of TNFα , increase cAMP levels, and inhibit phosphodiesterase.

In particular, the invention pertains to (a) a 2-(2,6-dioxo-3-fluoropiperidin-3-yl)-isoindoline of the formula:

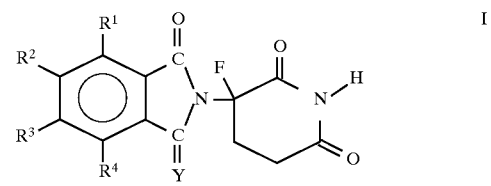

in which

Y is oxygen or $H_2$ and each of $R^1$, $R^2$, $R^3$, and $R^4$, independently of the others, is hydrogen, halo, alkyl of 1 to 4 carbon atoms, alkoxy of 1 to 4 carbon atoms, or amino, and (b) the acid addition salts of said 2-(2,6-dioxo-3-fluoropiperidin-3-yl)-isoindolines which contain a nitrogen atom capable of being protonated.

Unless otherwise defined, the term alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy.

The compounds of Formula I are used, under the supervision of qualified professionals, to inhibit the undesirable effects of TNFα and inhibit phosphodiesterase. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The compounds of Formula I are readily prepared through a number of routes. In a first embodiment, the ring nitrogen of a 2-(2,6-dioxopiperidin-3-yl)-isoindoline of Formula II is protected with a conventional amino protecting group to yield a protected 2-(2,6-dioxopiperidin-3-yl)-isoindoline of Formula III. This is then fluorinated to yield a protected 2-(2,6-dioxo-3-fluoropiperidin-3-yl)-isoindoline of Formula IV, following which removal of the protecting group yields the compounds of Formula V:

of $R^1$, $R^2$, $R^3$, and $R^4$ is amino, it too should be protected prior to the fluorination step.

Some of the compounds of Formula II which are here utilized as intermediates are known, as for example 1,3-dioxo-2-(2,6-dioxopiperidin-3-yl)-4-aminoisoindoline and 1,3-dioxo-2-(2, 6-dioxopiperidin-3 -yl)-5-aminoisoindoline. See, e.g., Jönsson, *Acta Pharma. Succica,* 9, 521–542 (1972). Others are described in copending application Ser. No. 08/701,494, U.S. Pat. No. 5,798,368 the disclosure of which is incorporated herein by reference, or can be prepared by methods analogous thereto.

The fluorination can be effected with a variety of reagents, as for example, N-fluorobenzenesulfonimide, perchloryl fluoride, N-fluorobenzenedisulfonimide, and the like, in the presence of a strong base such as n-butyl lithium, sodium hydride, lithium diisopropylamide, and the like.

In a second method, an appropriately substituted glutamic acid diester of Formula VI is fluorinated to yield the correstponding fluoroglutamic acid diester of Formula VI. This is then converted to the fluorinated glutamic acid anhydride of Formula VIII which, in turn, is amidated to yield the compounds of Formula V:

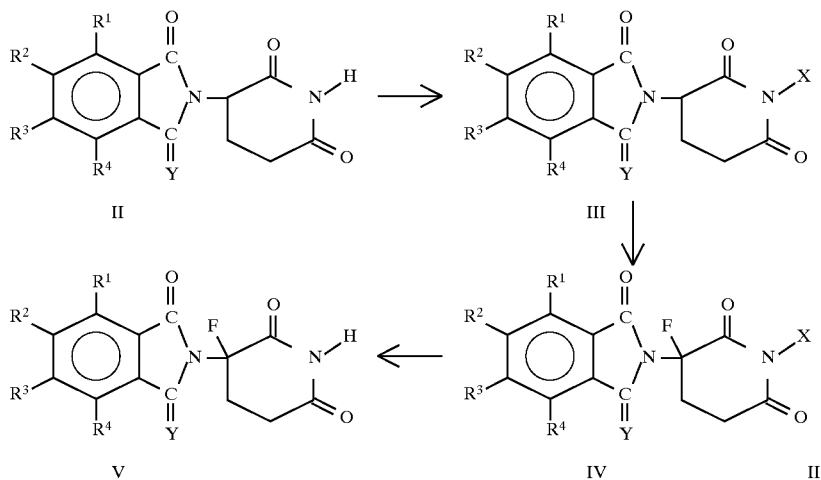

In the foregoin reactions, each of $R^1$, $R^2$, $R^3$, $R^4$, and Y are as defined above and X is amino protecting group. When any

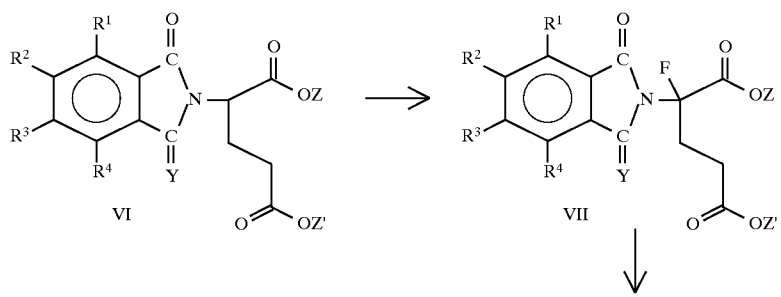

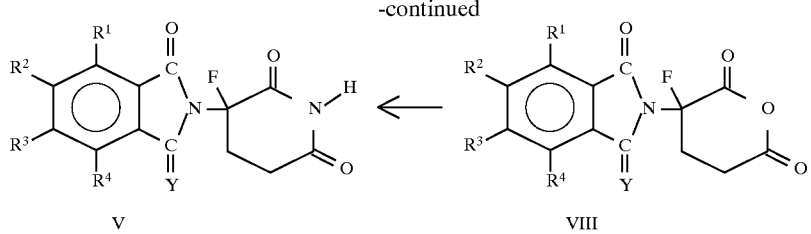

In the foregoin reactions, each of $R^1$, $R^2$, $R^3$, $R^4$, and Y are as defined above and Z and Z' are lower alkyl. Again when any of $R^1$, $R^2$, $R^3$, and $R^4$ is amino, it too should be protected prior to the fluorination step.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and N.Y., 1973; Greene, Th. W. "Protective Groups in Organic Synthesis", Wiley, N.Y. 1981; "The Peptides", Vol. I, Schröder and Lubke, Academic Press, London and N.Y., 1965; "Methoden der organischen Chemie", Houben-Weyl, 4th Edition, Vol.15/I, Georg Thieme Verlag, Stuttgart 1974, the disclosures of which are incorporated herein by reference.

In any of the foregoing reactions, a nitro compound can be employed with the nitro group being converted to an amino group by catalytic hydrogenation. Alternatively, a protected amino group can be cleaved to yield the corresponding amino compound. An amino group can be protected as an amide utilizing an acyl group which is selectively removable under mild conditions, especially benzyloxycarbonyl, formyl, or a lower alkanoyl group which is branched in 1- or α position to the carbonyl group, particularly tertiary alkanoyl such as pivaloyl, a lower alkanoyl group which is substituted in the position α to the carbonyl group, as for example trifluoroacetyl.

The carbon atom to which the depicted fluorine atom is bound in the compounds of Formula I constitutes a center of chirality, thereby giving rise to optical isomers:

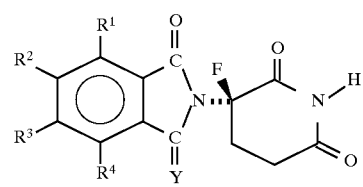

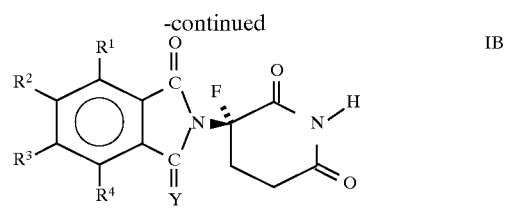

Both the racemates of these isomers and the individual isomers themselves, as well as diastereomers when a second chiral center is present, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid or base, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compound of Formula I which contain a group capable of being protonated; e.g., amino. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Particularly preferred compounds include 1,3-dioxo-2-(2,6-dioxo-3-fluoropiperidin-3-yl)-isoindoline, 1,3-dioxo-2-(2,6-dioxo-3-fluoropiperidin-3-yl)-4-aminoisoindoline, 1,3-dioxo-2-(2,6-dioxo-3-fluoropiperidin-3-yl)-5-aminoisoindoline, 1,3-dioxo-2-(2,6-dioxo-3-fluoropiperidin-3-yl)-4-methylisoindoline, 1,3-dioxo-2-(2,6-dioxo-3-fluoropiperidin-3-yl)-5-methylisoindoline, 1-oxo-2-(2,6-dioxo-3-fluoropiperidin-3-yl)-5-methylisoindoline, 1-oxo-2-(2,6-dioxo-3-fluoropiperidin-3-yl)-4-methylisoindoline, 1,3-dioxo-2-(2,6-dioxo-3-fluoropiperidin-3-yl)-4,5,6,7-tetrafluoroisoindoline, 1,3-dioxo-2-(2,6-dioxo-3-fluoropiperidin-3-yl)-4,5,6,7-tetrachloroisoindoline, 1,3-dioxo-2-(2,6-dioxo-3-fluoropiperidin-3-yl)-4,5,6,7-tetramethylisoindoline, 1,3-dioxo-2-(2,6-dioxo-3-fluoropiperidin-3-yl)-4,5,6,7-tetramethoxyisoindoline, 1-oxo-2-(2,6-dioxo-3-fluoropiperidin-3-yl)-5-aminoisoindoline, 1-oxo-2-(2,6-dioxo-3-fluoropiperidin-3-yl)-isoindoline, 1-oxo-2-(2,6-dioxo-3-fluoropiperidin-3-yl)-4-aminoisoindoline, 1-oxo-2-(2,6-dioxo-3-fluoropiperidin-3-yl)-4,5,6,7-tetrafluoroisoindoline, 1-oxo-2-(2,6-dioxo-3-fluoropiperidin-3-yl)- 4,5,6,7-tetrachloroisoindoline, 1-oxo- 2-(2,6-dioxo-3-fluoropiperidin-3-yl)-4,5,6,7-tetramethylisoindoline, and 1-oxo-2-(2,6-dioxo-3-fluoropiperidin-3-yl)-4,5,6,7-tetramethoxyisoindoline. Of these, 1,3-dioxo-2-(2,6-dioxo-3-fluoropiperidin-3-yl)-isoindoline and 1-oxo-2-(2,6-dioxo-3-fluoropiperidin-3-yl)-isoindoline are particularly preferred.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Enzyme-linked immunosorbent assays for TNFα can be performed in a conventional manner. PBMC is isolated from normal donors by Ficoll-Hypaque density centrifugation. Cells are cultured in RPMI supplemented with 10% AB+ serum, 2 mM L-glutamine, 100 U/mL penicillin, and 100 mg/mL streptomycin. Drugs are dissolved in dimethylsulfoxide (Sigma Chemical) and further dilutions are done in supplemented RPML. The final dimethylsulfoxide concentration in the presence or absence of drug in the PBMC suspensions is 0.25 wt %. Drugs are assayed at half-log dilutions starting at 50 mg/mL. Drugs are added to PBMC ($10^6$ cells/mL) in 96 wells plates one hour before the addition of LPS. PBMC ($10^6$ cells/mL) in the presence or absence of drug are stimulated by treatment with 1 mg/mL of LPS from *Salmonella minnesota* R595 (List Biological Labs, Campbell, Calif.). Cells are then incubated at 37° C. for 18–20 hours. Supernatants are harvested and assayed immediately for TNFα levels or kept frozen at −70° C. (for not more than 4 days) until assayed. The concentration of TNFα in the supernatant is determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1 \times 10^6$ cells /mL and collected by centrifugation. A cell pellet of $1 \times 10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β3-aminoethyl ether)-N,N,N',N'-tetraacetic acid (EGTA), 1 μM phenylmethylsulfonyl fluoride (PMSF), and 1 μg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity −/+ rolipram. Fractions containing phosphodiesterase activity (rolipram sensitive) are pooled and aliquoted for later use.

The phosphodiesterase assay is carried out based on procedure described by Hill and Mitchell. The assay is carried out in a total volume of 100 μl containing various concentration of the test compounds, 50 mM Tris-HCl, pH 7.5, 5 mM magnesium chloride and 1 μM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 10 μl 10 mg/mL snake venom for 15 min at 30° C. Unused substrate then is removed by adding 200 μl of a quaternary ammonium ion exchange resin (AG1-X8, BioRad) for 15 minutes. Samples then are spun at 3000 rpm, 5 min and 50 μl of the aqueous phase are taken for counting. Each data point is carried out in duplicate and activity is expressed as percentage of control. The $IC_{50}$ of the compound then is determined from dose response curves of a minimum of three independent experiments.

The following examples will serve to further typify the nature of this invention but should not be construed as a limitation in the scope thereof, which scope is defined solely by the appended claims.

EXAMPLE 1

To a stirred suspension of 1,3-dioxo-2-(2,6-dioxopiperidin-3-yl)isoindoline (2.0 g, 7.75 mmol) and di-tert.-butyl dicarbonate (1.86 g, 8.52 mmol) in 1,4-dioxane (3.0 mL) is added dimethylaminopyridine (1.00 mg) at room temperature. The solution is stirred at room temperature for 18 hours and the solvent then removed in vacuo. The residue is stirred with ether (30 mL) for 30 minutes, filtered, and washed with ether to give 1,3-dioxo-2-(1-tert.-butoxycarbonyl-2,6-dioxopiperidin-3-yl)isoindoline.

EXAMPLE 2

Similarly to the procedure of Example 1, there are respectively obtained from 1,3-dioxo-2-(2,6-dioxopiperidin-3-yl)-4,5,6,7-tetrafluoroisoindoline, 1,3-dioxo-2-(2,6-dioxopiperidin-3-yl)- 4,5,6,7-tetrachloroisoindoline, 1,3-dioxo-2-(2,6-dioxopiperidin-3-yl)-4,5,6,7- tetramethylisoindoline, 1,3-dioxo-2-(2,6-dioxopiperidin-3-yl)-4,5,6,7-tetramethoxyisoindoline, 1-oxo-2-(2,6-dioxopiperidin-3-yl)-isoindoline, 1-oxo-2-(2,6-dioxopiperidin-3-yl)-4,5,6,7-tetrafluoroisoindoline, 1-oxo-2-(2,6-dioxopiperidin-3-yl)- 4,5,6,7-tetrachloroisoindoline, 1-oxo-2-(2,6-dioxopiperidin-3-yl)- 4,5,6,7-tetramethylisoindoline, 1,3-dioxo-2-(2,6-dioxopiperidin-3-yl)-4-methylisoindoline, 1,3-dioxo-2-(2,6-dioxopiperidin-3-yl)-5-methylisoindoline, 1-oxo-2-(2,6-dioxopiperidin-3-yl)-5-methylisoindoline, 1-oxo-2-(2,6-dioxopiperidin-3-yl)-4-methylisoindoline, and 1-oxo-2-(2,6-dioxopiperidin-3-yl)-4,5,6,7-tetramethoxyisoindoline, the compounds 1,3-dioxo-2-(1-tert.-butoxycarbonyl-2,6-dioxopiperidin-3-yl)-4,5,6,7-tetrafluoroisoindoline, 1,3-dioxo-2-(1-tert.-butoxycarbonyl-2,6-dioxopiperidin-3-yl)-4,5,6,7-tetrachloroisoindoline, 1,3-dioxo-2-(1-tert.-butoxycarbonyl-2,6-dioxopiperidin-3-yl)-4,5,6,7-tetramethylisoindoline, 1,3-dioxo-2-(1-tert.-butoxycarbonyl-2,6-dioxopiperidin-3-yl)-4,5,6,7-tetramethoxyisoindoline, 1-oxo-2-(1-tert. -butoxycarbonyl-2,6-dioxopiperidin-3-yl)-isoindoline, 1 -oxo-2-(1 -tert. -butoxycarbonyl-2,6-dioxopiperidin-3-yl)-4,5,6,7-tetrafluoroisoindoline, 1 -oxo-2-(1 -tert.-butoxycarbonyl-2,6-dioxopiperidin-3-yl)-4,5,6,7-tetrachloroisoindoline, 1 -oxo-2-(1 -tert.-butoxycarbonyl-2,6-dioxopiperidin-3-yl)-4,5,6,7-tetramethylisoindoline, 1,3-dioxo-2-(1-tert.-butoxycarbonyl-2,6-dioxopiperidin-3-yl)-4-methylisoindoline, 1,3 -dioxo-2-(1 -tert. -butoxycarbonyl-2,6-dioxopiperidin-3-yl)-5-methylisoindoline, 1-oxo-2-(1 -tert. -butoxycarbonyl-2,6-dioxopiperidin-3-yl)-5-methylisoindoline, 1-oxo-2-(1-tert.-butoxycarbonyl-2,6-dioxopiperidin-3-yl)-4-methylisoindoline, and 1-oxo-2-(1-tert.-butoxycarbonyl-2,6-dioxopiperidin-3-yl)-4,5,6,7-tetramethoxyisoindoline Similarly utilizing equivalent amounts of 1,3-dioxo-2-(2,6-dioxopiperidin-3-yl)-4-aminoisoindoline, 1,3-dioxo-2-(2,6-dioxopiperidin-3-yl)-5-aminoisoindoline, 1-oxo-2-(2,6-dioxopiperidin-3-yl)-5-aminoisoindoline, and 1-oxo-2-(2,6-dioxopiperidin-3-yl)-4-aminoisoindoline, but utilizing 3.72 g of di-tert.-butyl dicarbonate in the procedure of Example 1, there are respectively obtained 1,3-dioxo-2-(1-tert.-butoxycarbonyl-2,6-dioxopiperidin-3-yl)-4-(1-tert.-butoxycarbonylamino)-isoindoline, 1,3-dioxo-2-(1 -tert.-butoxycarbonyl-2,6-dioxopiperidin-3-yl)-5-(1-tert.-butoxycarbonylamino)-isoindoline, 1-oxo-2-(1-tert. -butoxycarbonyl-2,6-dioxopiperidin-3-yl)-5-(1 -tert.-butoxycarbonylamino)-isoindoline, and 1-oxo-2-(1-tert.-butoxycarbonyl-2,6-dioxopiperidin-3-yl)-4-(1-tert.-butoxycarbonylamino)-isoindoline.

EXAMPLE 3

To a stirred solution of 1,3-dioxo-2-(1-tert.-butoxycarbonyl-2,6-dioxopiperidin-3-yl)isoindoline (1.0 g, 2.8 mmol) in tetrahydrofuran (10 mL) is added n-butyl lithium (1.2 mL, 3.0 mmol, 2.5M) at −78° C. After 20 minutes, N-fluorobenzenesulfonimide (0-8 g, 3.2 mmol) is added to the mixture. The mixture is allowed to reach room temperature and the solvent then removed in vacuo. The residue is stirred with ethyl acetate (10 mL) and lN hydrochloric acid (10 mL) for one hour. The organic layer is separated and the solvent removed in vacuo to yield 1,3-dioxo-2-(2,6-dioxo-3-fluoropiperidin-3-yl)isoindoline which can be further purified through chromatography.

EXAMPLE 4

The procedure of Example 3 is followed, substituting, however, 0.76 g of N-fluorobenzenedisulfonimide for the 0.8 g of N-fluorobenzenesulfonimide. There is thereby obtained 1,3-dioxo-2-(2,6-dioxo-3-fluoropiperidin-3-yl) isoindoline which can be further purified through column chromatography.

EXAMPLE 5

To a stirred solution of 1,3-dioxo-2-(1-tert.-butoxycarbonyl-2,6-dioxopiperidin-3-yl)isoindoline (1.0 g. 2.8 mmol) in tetrahydrofuran (10 mL) is added lithium diisopropylamide (1.5 mL, 3.0 mmol, 2M) at . After 30 minutes, perchloryl fluoride (5 mmol) is bubbled into the mixture. The mixture is allowed to reach room temperature and the solvent then removed in vacuo. The residue is stirred with ethyl acetate (10 mL) and lN hydrochloric acid (10 mL) for one hour. The organic layer is separated and the solvent removed in vacuo to yield 1,3-dioxo-2-(2,6-dioxo-3-fluoropiperidin-3-yl)isoindoline which can be further purified through chromatography.

EXAMPLE 6

To a stirred solution of 1,3-dioxo-2-(1-tert.-butoxycarbonyl-2,6-dioxopiperidin-3-yl)-isoindoline (1.0 g. 2.8 mmol) in dimethylformamide (10 mL) is added sodium hydride (112 mg, 2.8 mmol, 60%) at room temperature. After about 30 minutes, perchloryl fluoride (5 mmol) is bubbled into the mixture . The mixture is stirred with methylene chloride (10 mL) and lN hydrochloric acid (10 mL) for one hour. The organic layer is separated 30 and the solvent removed in vacuo to yield 1,3-dioxo-2-(2,6-dioxo-3-fluoropiperidin-3-yl)isoindoline which can be further purified through chromatography.

EXAMPLE 7

To a stirred solution of 1,3-dioxo-2-(1-tert.-butoxycarbonyl-2,6-dioxopiperidin-3-yl)isoindoline (1.0 g, 2.8 mmol) and tetramethylethylene diamine (0.5 g, 4.3 mmol) in tetrahydrofuran (10 mL) is added n-butyl lithium (1.2 mL, 3.0 mmol, 2.5 M) at −78° C. After 30 minutes, N-fluorobenzenesulfonimide (0-8 g, 3.2 mmol) is added to the mixture. The mixture is allowed to reach room temperature and the solvent then removed in vacuo. The residue is stirred with ethyl acetate (10 mL) and lN hydrochloric acid (10 mL) for one hour. The organic layer is separated and the solvent removed in vacuo to yield 1,3-dioxo-2-(2,6-dioxo-3-fluoropiperidin-3-yl)isoindoline which can be further purified through column chromatography.

EXAMPLE 8

Starting with each of 1,3-dioxo-2-(1-tert.-butoxycarbonyl-2,6-dioxopiperidin-3-yl)-4-(1-tert.-butoxycarbonylamino)-isoindoline, 1,3-dioxo-2-(1-tert.-butoxycarbonyl-2,6-dioxopiperidin-3-yl)-5-(1-tert.-butoxycarbonylamino)-isoindoline, 1,3-dioxo-2-(1-tert.-butoxycarbonyl-2,6-dioxopiperidin-3-yl)-4,5,6,7-tetrafluoroisoindoline, 1,3-dioxo-2-(1-tert.-butoxycarbonyl-2,6-dioxopiperidin-3-yl)- 4,5,6,7-tetrachloroisoindoline, 1,3-dioxo-2-(1-tert.-butoxycarbonyl-2,6-dioxopiperidin-3-yl)-4,5,6,7-tetramethylisoindoline, 1,3-dioxo-2-(1-tert.-butoxycarbonyl-2,6-dioxopiperidin-3-yl)-4,5,6,7-tetramethoxyisoindoline, 1-oxo-2-(1-tert.-butoxycarbonyl-2,6-dioxopiperidin-3-yl)-5-(1-tert.-butoxycarbonylamino)-isoindoline, 1-oxo-2-(1-tert.-butoxycarbonyl-2,6-dioxopiperidin-3-yl)-isoindoline, 1-oxo-2-(1-tert.-butoxycarbonyl-2,6-dioxopiperidin-3-yl)-4-(1-tert.-butoxycarbonylamino)-isoindoline, 1-oxo-2-(1-tert.- butoxycarbonyl-2,6-dioxopiperidin-3-yl)-4,5,6,7-tetrafluoroisoindoline, 1-oxo-2-(l-tert.-butoxycarbonyl-2,6-dioxopiperidin-3-yl)- 4,5,6,7-tetrachloroisoindoline, 1-oxo-2-(1-tert.-butoxycarbonyl-2,6-dioxopiperidin-3-yl)- 4,5,6,7-tetramethylisoindoline, 1,3-dioxo-2-(1-tert.-butoxycarbonyl-2,6-dioxopiperidin-3 -yl)-4-methylisoindoline, 1,3-dioxo-2-(1-tert.-butoxycarbonyl-2,6-dioxopiperidin-3-yl)-5-methylisoindoline, 1-oxo-2-(1-tert.- butoxycarbonyl-2,6-dioxopiperidin- 3-yl)- 5-methylisoindoline, 1-oxo-2-(1-tert.-butoxycarbonyl-2,6-dioxopiperidin-3- yl)-4-methylisoindoline, and 1-oxo-2-(1-tert.-butoxycarbonyl-2,6-dioxopiperidin-3-yl)-4,5,6,7-tetramethoxyisoindoline, there are respectively obtained by following the procedures of Examples 3, 4, 5, 6, or 7, 1,3-dioxo-2-(2,6-dioxo-3-fluoropiperidin-3-yl)-4-aminoisoindoline, 1,3-dioxo-2-(2,6-dioxo-3-fluoropiperidin-3-yl)-5-aminoisoindoline, 1,3-dioxo-2-(2,6-dioxo-3-fluoropiperidin-3-yl)-4,5,6,7-tetrafluoroisoindoline, 1,3-dioxo-2-(2,6-dioxo-3-fluoropiperidin-3-yl)- 4,5,6,7-tetrachloroisoindoline, 1,3-dioxo-2-(2,6-dioxo-3-fluoropiperidin-3-yl)-4,5,6,7-tetramethylisoindoline, 1,3-dioxo-2-(2,6-dioxo-3-fluoropiperidin-3-yl)-4,5,6,7-tetramethoxyisoindoline, 1-oxo-2-(2,6-dioxo-3-fluoropiperidin-3-yl)-5-aminoisoindoline, 1-oxo-2-(2,6-dioxo-3-fluoropiperidin-3-yl)-isoindoline, 1-oxo-2-(2,6-dioxo-3-fluoropiperidin-3-yl)-4-aminoisoindoline, 1-oxo-2-(2,6-dioxo-3-fluoropiperidin-3-yl)-4,5,6,7-tetrafluoroisoindoline, 1-oxo-2-(2,6-dioxo-3-fluoropiperidin-3-yl)- 4,5,6,7-tetrachloroisoindoline, 1-oxo-2-(2,6-dioxo-3-fluoropiperidin-3-yl)- 4,5,6,7-tetramethylisoindoline, 1,3-dioxo-2-(2,6-dioxo-3-fluoropiperidin-3-yl)-4-methylisoindoline, 1,3-dioxo-2-(2,6-dioxo-3-fluoropiperidin-3-yl)-5-methylisoindoline, 1-oxo-2-(2,6-dioxo-3-fluoropiperidin-3-yl)-5-methylisoindoline, 1-oxo-2-(2,6-dioxo-3-fluoropiperidin-3-yl)-4-methylisoindoline, and 1-oxo-2-(2,6-dioxo-3-fluoropiperidin-3-yl)-4,5,6,7-tetramethoxyisoindoline.

EXAMPLE 9

Part A.

A solution of L-glutamic acid dimethyl ester (2.6 g, 14.8 mmol), isoamyl nitrite (2.13 mL, 15.9 mmol) and acetic acid (0.22 mL) in benzene (150 mL) is heated to reflux for one hour. The solution is washed with 1N aqueous sulfuric acid, water, saturated sodium hydrogen carbonate solution, water and brine (50 mL each). The solvent is removed in vacuo to yield dimethyl 2-diazopentane-1,5-dioate which can be further purified by column chromatography.

Part B.

To a cold solution of 5 mL of 70% hydrogen fluoride in pyridine and 1.2 g (6.7 mmol) N-bromosuccinimide in 10 mL of ether is added a solution of dimethyl 2-diazopentane-1,5-dioate (1.1 g, 5.9 mmol) in ether (10 mL) at 0C. The mixture is stirred at 0° C. for 30 minutes The solution is washed with water (20 mL), brine (20 mL) and dried over sodium sulfate. The solvent is removed in vacuo to yield dimethyl 2-bromo-2-fluoropentane-1,5-dioate which can be further purified by column chromatography.

Part C.

A mixture of dimethyl 2-bromo-2-fluoropentane-1,5-dioate (1.0 g, 3.8 mmol) and potassium phthalimide (0.79 g, 4.3 mmol) in dimethylformamide (10 mL) is heated at 80° C. for 3 hours. The solvent is removed in vacuo and the residue is stirred with ethyl acetate (50 mL) for 10 minutes. The organic layer is washed with water and brine (20 mL each), and dried over sodium sulfate. The solvent is removed in vacuo to yield dimethyl 2-(1,3-dioxoisoindolin-2-yl)-2-fluoropenta-1,5-dioate which can be further purified by column chromatography.

Part D.

A mixture of dimethyl 2-(1,3-dioxoisoindolin-2-yl)-2-fluoropenta-1,5-dioate (1.3 g, 4.0 mmol), methanol (10 mL) and 4N hydrochloric acid (10 mL) is heated at 80° C. or one hour. The solvent is removed in vacuo to yield 2-fluoro-2-(1,3-dioxoisoindolin-2-yl)-propane-1,3-dicarboxylic acid. This is dissolved in acetic anhydride (20 mL) and the solution heated at reflux for 30 minutes. The solvent is remove in vacuo to yield 2-fluoro-2-(1,3-dioxoisoindolin-2-yl)-propane-1,3-dicarboxylic acid anhydride which is mixed with ammonia in methanol (35 mL, 2M) and stirred at room temperature for 18 hours. The solvent is then removed in vacuo and the residue is stirred with methylene chloride (50 mL) for 10 minutes. The organic layer is washed with water and brine (40 mL each), and dried over sodium sulfate. The solvent is removed in vacuo and the residue is heated at reflux with carbonyl diimidazole (0.65 g. 4 mmol) and dimethylaminopyridine (50 mg) in tetrahydrofuran (30 mL) for 18 hours. 1,3-Dioxo-2-(2,6-dioxo-3-fluoropiperidin-3-yl)isoindoline is isolated extraction with ethyl acetate and further purified by chromatography.

EXAMPLE 10

A stirred mixture of L-glutamic acid dimethyl ester (2.0 g, 11.4 mmol) and phthalic anhydride (1.7 g, 11.4 mmol) in acetic acid (30 mL) is heated to refluxed for one hour. The solvent is removed in vacuo to yield dimethyl 2-(1,3-dioxoisoindolin-2-yl)-pentane-1,5-dioate which is further purified through chromatography.

To a stirred solution of dimethyl 2-(1,3-dioxoisoindolin-2-yl)-pentane-1,5-dioate (1.0 g, 3.3 mmol) and tetramethylethylene diamine (0.5 g, 4.3 mmol) in tetrahydrofuran (10 mL) is added 2.5M n-butyl lithium (1.6 mL, 4 mmol,) at −79° C. After 30 minutes, N-fluorobenzenesulfonimide (1 g, 3.2 mmol) is added to the mixture which then is allowed to reach room temperature. The solvent is removed in vacuo and the residue is stirred with methylene chloride (100 mL) for 10 minutes. The organic layer is washed with water and brine (30 mL each), and dried over sodium sulfate. The solvent is removed in vacuo to yield dimethyl 2-(1,3-dioxoisoindolin-2-yl)-2-fluoropentane-1,5-dioate which is further purified by chromatography and converted to 1,3-dioxo-2-(2,6-dioxo-3-fluoropiperidin-3-yl)isoindoline as described above in Part D of Example 9.

EXAMPLE 11

A stirred mixture of ethyl bromofluoroacetate (1.0 g, 5.4 mmol) and potassium phthalide (1.0 g, 5.4 mmol) in dimethylformamide (10 mL) is heated at 80° C. for 3 hours. The mixture is stirred with ether (50 mL) and water (50 mL) and the organic layer then washed with water and brine (30 mL each), and dried over sodium sulfate. The solvent is removed in vacuo to give ethyl 2-(1,3-dioxoisoindolin-2-yl)-2-fluoroacetate which is further purified through chromatography.

To a stirred solution of ethyl 2-(1,3-dioxoisoindolin-2-yl)-2-fluoroacetate (0.80 g, 3.2 mmol) in tetrahydrofuran (30 mL) is added lithium diisopropylamide (1.7 mL, 3.4 mmol, 2M) at −78° C. After 30 minutes, t-butyl acrylate (0.42 g, 3.2 mmol) is added to the mixture which is allowed to reach room temperature. The solvent is removed in vacuo and the residue stirred with methylene chloride (50 mL) and water (30 mL) for 10 min. The organic layer is washed with brine (30 mL), and dried over sodium sulfate. The solvent is removed in vacuo to give tert-butyl 4-(1,3-dioxoisoindolin-2-yl)-4-fluoro-4-ethoxycarbonylbutanoate which is further purified by column chromatography.

A solution of tert-butyl 4-(1,3-dioxoisoindolin-2-yl)-4-fluoro-4-ethoxycarbonylbutanoate (1.1 g, 3 mmol) and trifluoroacetic acid (5 mL) in methylene chloride (5 mL) is stirred for 18 hours and then with methylene chloride (50 mL) for 10 min. The organic layer is washed with water and brine (30 mL each), and dried over sodium sulfate. The solvent is removed in vacuo to yield 4-(1,3-dioxoisoindolin-2-yl)-4-(ethoxycarbonyl)-4-fluorobutanoic acid which can be purified by chromatography or used in the next step without further purification.

A mixture of 4-(1,3-dioxoisoindolin-2-yl)-4-(ethoxycarbonyl)-4-fluorobutanoic acid (0.9 g, 2.8 mmol), carbonyl diimidazole (0.46 g, 2.8 mmol) and dimethylaminopyrimidine (0.68 g, 5.6 mmol) in tetrahydrofuran (30 mL) is heated at reflux for 18 hours. The solvent is removed in vacuo and the residue is stirred with methylene chloride (50 mL) for 10 minutes. The organic layer is washed with water and brine (40 mL each) and dried over sodium sulfate. The solvent is removed in vacuo to give 1,3-dioxo-2-(2,6-dioxo-3-fluoropiperidin-3-yl)isoindoline which is further purified by column chromatography.

EXAMPLE 12

Tablets, each containing 50 mg of 1,3-dioxo-2-(2,6-dioxo-3-fluoropiperidin-3-yl)-isoindoline, can be prepared in the following manner:

| Constituents (for 1000 tablets) | |
| --- | --- |
| 1,3-dioxo-2-(2,6-dioxo-3-fluoropiperidin-3-yl)-isoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 13

Tablets, each containing 100 mg of 1-oxo-2-(2,6-dioxo-3-fluoropiperidin-3-yl)-isoindoline, can be prepared in the following manner:

| Constituents (for 1000 tablets) | |
| --- | --- |
| 1-oxo-2-(2,6-dioxo-3-fluoropiperidin-3-yl)-isoindoline | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 14

Tablets for chewing, each containing 75 mg of 1-oxo-2-(2,6-dioxo-3-fluoropiperidin-3-yl)-isoindoline, can be prepared in the following manner:

| Composition (for 1000 tablets) | |
| --- | --- |
| 1-oxo-2-(2,6-dioxo-3-fluoropiperidin-3-yl)-isoindoline | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 1-Oxo-2-(2,6-dioxo-3-fluoropiperidin-3-yl)-isoindoline, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 15

Tablets, each containing 10 mg 1,3-dioxo-2-(2,6-dioxo-3-fluoropiperidin-3-yl)-4,5,6,7-tetrafluoroisoindoline, can be prepared in the following manner:

| Composition (for 1000 tablets) | |
| --- | --- |
| 1,3-dioxo-2-(2,6-dioxo-3-fluoropiperidin-3-yl)-4,5,6,7-tetrafluoroisoindoline | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 16

Gelatin dry-filled capsules, each containing 100 mg of 1-oxo-2-(2,6-dioxo-3-fluoropiperidin-3-yl)-5-aminoisoindoline, can be prepared in the following manner:

| Composition (for 1000 capsules) | |
|---|---|
| 1-oxo-2-(2,6-dioxo-3-fluoropiperidin-3-yl)-5-aminoisoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxo-3-fluoropiperidin-3-yl)-5-aminoisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 17

A 0.2% injection or infusion solution can be prepared, for example, in the following manner:

| | |
|---|---|
| 1,3-dioxo-2-(2,6-dioxo-3-fluoropiperidin-3-yl)-5-aminoisoindoline hydrochloride | 5.0 g |
| sodium chloride | 22.5 g |
| phosphate buffer pH 7.4 | 300.0 g |
| demineralized water | to 2500.0 mL |

1,3-Dioxo-2-(2,6-dioxo-3-fluoropiperidin-3-yl)-5-aminoisoindoline hydrochloride is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

What is claimed is:

1. A compound selected from the group consisting of
   (a) a 2-(2,6-dioxo-3-fluoropiperidin-3-yl)-isoindoline of the formula:

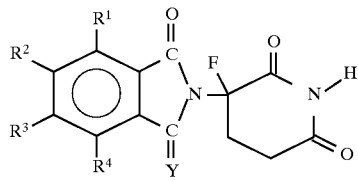

I in which
   Y is oxygen or $H_2$ and
   each of $R^1$, $R^2$, $R^3$, and $R^4$, independently of the others, is hydrogen, halo, alkyl of 1 to 4 carbon atoms, alkoxy of 1 to 4 carbon atoms, or amino, and
   (b) the acid addition salts of said 2-(2,6-dioxo-3-fluoropiperidin-3-yl)-isoindolines which contain a nitrogen atom capable of being protonated.

2. The compound according to claim 1 in which $R^1$, $R^2$, $R^3$, and $R^4$ are hydrogen.

3. A compound according to claim 1 in which $R^1$, $R^2$, $R^3$, and $R^4$ are the same and each is chloro, fluoro, methyl, or methoxy.

4. A compound according to claim 1 in which $R^3$ is amino, and R', $R^2$, and $R^4$ are hydrogen.

5. A compound according to claim 1 in which $R^4$ is amino, and $R^1$, $R^2$, and $R^3$ are hydrogen.

6. A compound according to claim 1 in which $R^3$ is methyl, and $R^1$, $R^2$, and $R^4$ are hydrogen.

7. A compound according to claim 1 in which $R^4$ is methyl, and $R^1$, $R^2$, and $R^3$ are hydrogen.

8. The compound according to claim 1 which is 1,3-dioxo-2-(2,6-dioxo-3-fluoropiperidin-3-yl)-isoindoline.

9. The compound according to claim 1 which is 1,3-dioxo-2-(2,6-dioxo-3-fluoropiperidin-3-yl)-4-aminoisoindoline.

10. The compound according to claim 1 which is 1,3-dioxo-2-(2,6-dioxo-3-fluoropiperidin-3-yl)-5-aminoisoindoline.

11. The compound according to claim 1 which is 1,3-dioxo-2-(2,6-dioxo-3-fluoropiperidin-3-yl)-4,5,6,7-tetrafluoroisoindoline.

12. The compound according to claim 1 which is 1,3-dioxo-2-(2,6-dioxo-3-fluoropiperidin-3-yl)- 4,5,6,7-tetrachloroisoindoline.

13. The compound according to claim 1 which is 1,3-dioxo-2-(2,6-dioxo-3-fluoropiperidin-3-yl)- 4,5,6,7-tetramethylisoindoline.

14. The compound according to claim 1 which is 1,3-dioxo-2-(2,6-dioxo-3-fluoropiperidin-3-yl)-4,5,6,7-tetramethoxyisoindoline.

15. The compound according to claim 1 which is 1-oxo-2-(2,6-dioxo-3-fluoropiperidin-3-yl)-5-aminoisoindoline.

16. The compound according to claim 1 which is 1-oxo-2-(2,6-dioxo-3-fluoropiperidin-3-yl)-isoindoline.

17. The compound according to claim 1 which is 1-oxo-2-(2,6-dioxo-3-fluoropiperidin-3-yl)-4-aminoisoindoline.

18. The compound according to claim 1 which is l-oxo-2-(2,6-dioxo-3-fluoropiperidin-3-yl)-4,5,6,7-tetrafluoroisoindoline.

19. The compound according to claim 1 which is 1-oxo-2-(2,6-dioxo-3-fluoropiperidin-3-yl)-4,5,6,7-tetrachloroisoindoline.

20. The compound according to claim 1 which is 1-oxo-2-(2,6-dioxo-3-fluoropiperidin-3-yl)-4,5,6,7-tetramethylisoindoline.

21. The compound according to claim 1 which is 1-oxo-2-(2,6-dioxo-3-fluoropiperidin-3-yl)-4,5,6,7-tetramethoxyisoindoline.

22. The method of reducing undesirable levels of TNFα in a mammal which comprises administering thereto an effective amount of a compound according to claim 1.

23. A pharmaceutical composition comprising a quantity of a compound according to claim 1 sufficient upon administration in a single or multiple dose regimen to reduce levels of TNFα in a mammal in combination with a carrier.

* * * * *